United States Patent
Biesel et al.

[11] Patent Number: 5,814,279
[45] Date of Patent: Sep. 29, 1998

[54] CENTRIFUGE HAVING MARKER ELEMENTS

[75] Inventors: Wolfgang Biesel, Ottweiler; Stefan Kreber, Saarbrucken; Henning Brass, Homburg; Friedrich Witthaus, St. Wendel; Artur Meisberger, St. Wendel, all of Germany

[73] Assignee: Fresenius AG, Homburg, Germany

[21] Appl. No.: 597,443

[22] Filed: Feb. 2, 1996

[30] Foreign Application Priority Data

Feb. 3, 1995 [DE] Germany .................. 195 03 534.8

[51] Int. Cl.[6] .................................................. G01N 21/07
[52] U.S. Cl. ..................... 422/72; 422/100; 422/102; 436/45; 436/165; 436/177; 494/10; 356/428
[58] Field of Search ................... 422/67, 72, 101, 422/104, 102; 436/43, 50, 55, 45, 180, 164, 165, 177; 494/10; 356/244, 246, 427, 428

[56] References Cited

U.S. PATENT DOCUMENTS

| | | | |
|---|---|---|---|
| Re. 31,149 | 2/1983 | Ginsberg et al. | 422/64 |
| 3,555,184 | 1/1971 | Anderson | 436/45 |
| 3,576,441 | 4/1971 | Adams et al. | 436/45 |
| 3,744,974 | 7/1973 | Maddox et al. | 422/72 |
| 4,226,537 | 10/1980 | Colley | 356/427 |
| 4,446,106 | 5/1984 | Nelson et al. | 422/72 |
| 4,493,691 | 1/1985 | Calari | |
| 4,695,164 | 9/1987 | Zivitz et al. | 356/427 |
| 5,122,284 | 6/1992 | Braynin et al. | 210/782 |
| 5,186,896 | 2/1993 | Bouchee et al. | 422/72 |
| 5,260,598 | 11/1993 | Brass et al. | |
| 5,580,790 | 12/1996 | Wall et al. | 436/45 |

FOREIGN PATENT DOCUMENTS 1 325 536  8/1969  United Kingdom .

*Primary Examiner*—Long V. Le
*Attorney, Agent, or Firm*—Cushman Darby&Cushman IP Group of Pillsbury Madison & Sutro LLP

[57] ABSTRACT

A centrifuge has a drive unit, a separation chamber which can be inserted into the drive unit, and a scanning device for recognizing the position of the separation chamber which is rotated by the drive unit. The separation chamber is constructed as a disposable chamber and is provided with a marker element which is arranged in a scanning region extending annularly around the rotation axis of the chamber. The position of a phase boundary window is detected by sensing the position of the marker with a phase boundary detector portion of the scanning device whereby the chamber can be inserted into the drive unit in any position.

7 Claims, 4 Drawing Sheets

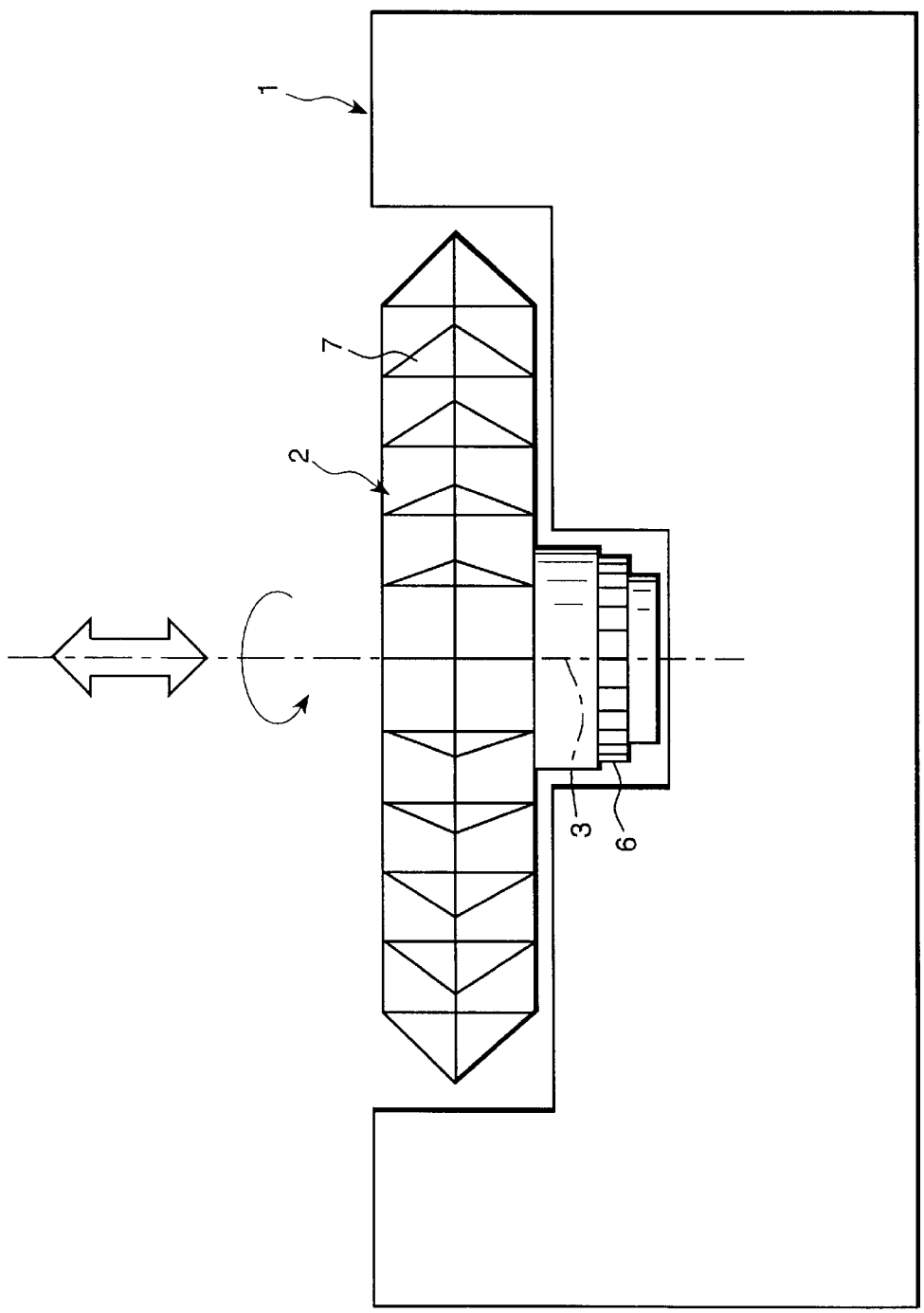

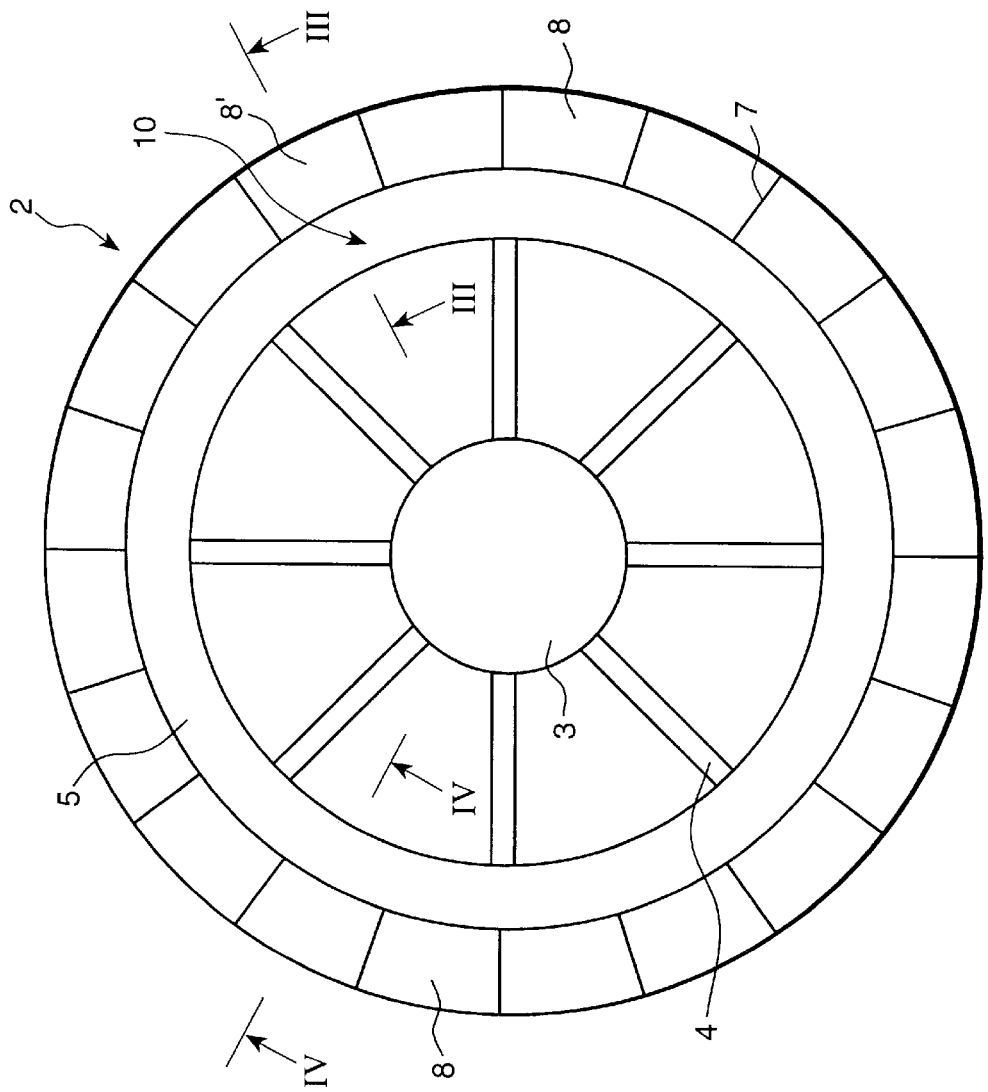

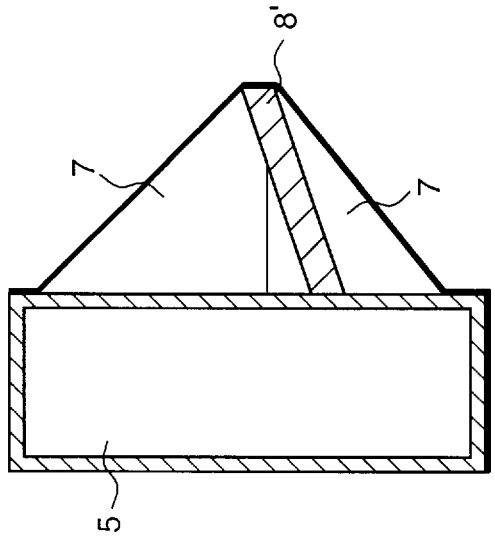
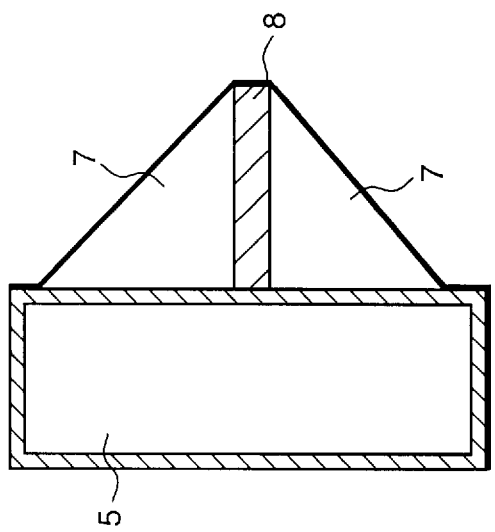

CENTRIFUGE HAVING MARKER ELEMENTS

BACKGROUND OF THE INVENTION

1. Field of the Invention

The invention relates to a centrifuge with a drive unit, a separation chamber which can be inserted into the drive unit, and a scanning device for recognizing the position of the separation chamber that can be rotated by the drive unit. The invention also relates to a process for recognizing the position of a separation chamber inserted into the drive unit of a centrifuge and set rotating by the drive unit.

2. The Prior Art

The known centrifuges for separating whole blood into its constituents have an essentially rotationally symmetrical separation chamber made from transparent material. The position of the separation boundary between the separated blood constituents in the rotating chamber is monitored in the known centrifuges using an optical phase boundary detector. To detect the phase boundary, a specific region of the separation chamber, i.e. the phase boundary window, is irradiated with a light source, whereby the light beams passing through the phase boundary window are detected by a light receiver arranged in fixed manner. Such devices are described in DE 33 01 113 or DE 41 32 965. In order to avoid the detection of error signals, irradiation of the separation chamber and evaluation of the values ascertained by the light detector can take place only when the phase boundary Window of the rotating chamber lies between light source and light receiver of the phase boundary detector. It is therefore necessary to determine the position of the phase boundary window relative to the phase boundary detector.

In general, disposable separation chambers are used with the known centrifuges for separating blood components. These are inserted into the drive unit of the centrifuge and can be replaced by a new chamber after use. The rotor of the drive unit housing the separation chamber is provided with a speed indicator in order to able to determine both the speed of the rotor and also the position of the rotor and thus the position of the phase boundary window of the separation chamber inserted into the rotor.

It is a disadvantage that the separation chamber of the known centrifuges may be inserted into the rotor of the drive unit only in a certain position. In fact, if the chamber is inadvertently inserted into the rotor upside down, the trigger signal is generated at a time when the phase boundary window of the chamber in displaced relative to the phase boundary detector. In this case incorrect values are transmitted to the evaluation unit.

SUMMARY OF THE INVENTION

It is the object of the invention to provide a centrifuge into whose drive unit the separation chamber can be inserted in any position and to provide a process which allows recognition of the position of a separation chamber which can be inserted in any position into the drive unit of a centrifuge.

The separation chamber of the centrifuge according to the invention is provided with a marker element which indicates a reference position of the chamber. A scanning device is also provided which scans the separation chamber to detect the marker element.

In order to be able to control the phase boundary detector device of the centrifuge, the position of the phase boundary window of the chamber can for example be characterized as the reference position using the marker element. Since the position of the phase boundary window is determined by a marker element on the chamber itself, the chamber can be inserted in any position into the drive unit of the centrifuge. The possibility of the phase boundary being wrongly adjusted as a result of an error by the operator of the centrifuge is thus excluded. It is therefore not necessary to give corresponding instructions or train personnel in charge of centrifuge operation. Operation of the centrifuge is also simplified since it is not necessary, when inserting the separation chamber into the drive unit, to ensure that the chamber is in a certain position.

The reference position of the separation chamber can in principle be marked in various ways. Both mechanical and optical scanning devices can be used in principle for recognizing the position of the chamber.

With the centrifuge according to the invention, scanning advantageously takes place using optical means. The optical scanning device for detecting the marker element has a light source, the light from which strikes the scanning region of the separation chamber, and a detector device which detects the light reflected by the separation chamber. The reference position can be ascertained from the change in the distribution of the light reflected by the separation chamber as a result of the rotation of the chamber, it being assumed that a certain light distribution on the separation chamber is characteristic of the reference position. Light distribution on the chamber can e.g. be ascertained using a detector device constructed as a camera. It is thus possible to map the entire separation chamber to recognize the position of the marker element. However, just a part of the separation chamber can also be scanned e.g. using a suitably arranged CCD line or a single photodiode.

It is of particular advantage that the marker element is formed only by an inclined segment in the scanning region of the separation chamber with the result that there is no need to make major, changes to the chamber. No additional operations are required for the construction of the marker element during manufacture of the disposable chamber. The marker element, which is an integral component of the separation chamber, thus creates no additional costs and also does not change the properties of the separation chamber as regards all parameters important for its use. Alternatively, the reference position can also be marked by an area having a lower reflectivity than the other parts of the chamber.

The detector device is expediently constructed as an optical detector and arranged in the beam path of the light reflected by the inclined chamber segment. The light is thus most strongly received by the detector device when it strikes the inclined chamber segment. Alternatively, it is also possible to arrange the detector device in such a manner that the detector device is arranged outside the beam path of the light reflected at the inclined chamber segment, but within the beam region of the light reflected at the other part of the scanning region. The output signal of the optical detector is then to be correspondingly ignored in order to be able to obtain a reference position signal.

A particular advantage of the optical scanning device of the centrifuge according to the invention is that the reflected light beam can be detected with the same light receiver which is also a component of the phase boundary detector. By arranging the components appropriately, the scanning region of the separation chamber can also be irradiated using the light source of the phase boundary detector. Thus no additional expenditure is required from the point of view of equipment (hardware).

A further development of the invention is to be seen in the transillumination of the separation chamber and the detection of the light shining through the chamber.

BRIEF DESCRIPTION OF THE DRAWINGS

An embodiment of the invention is described in more detail below with reference to the drawings.

These show:

FIG. 1 the centrifuge in schematic representation,

FIG. 2 the separation chamber which can be inserted into the drive unit of the centrifuge in top view, FIG. 3 a section through the separation chamber along the line III—III in FIG. 2 in enlarged representation, FIG. 4 a section along the line IV—IV in FIG. 2 in enlarged representation, FIG. 5 the beam path for position recognition at non-inclined segments of the separation chamber and FIG. 6 the beam path for position recognition at the inclined chamber segment.

DESCRIPTION OF A PREFERRED EMBODIMENT OF THE INVENTION

Figure 5:
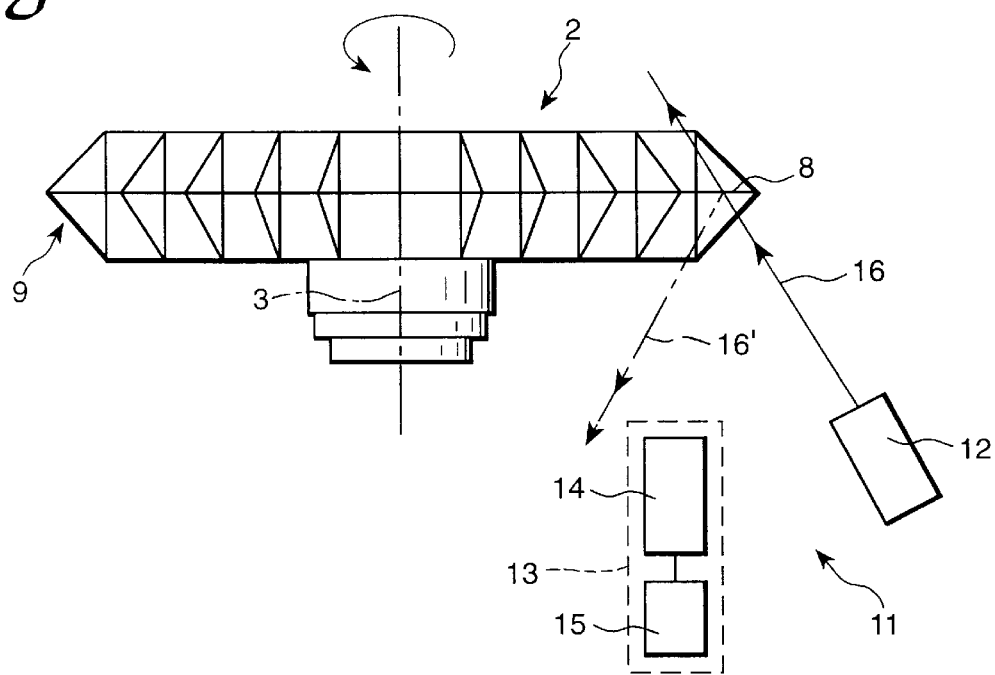

FIG. 1 shows the centrifuge according to the invention for separating whole blood into its constituents in schematic representation. The centrifuge consists of a drive unit 1 and a separation chamber 2 which can be inserted into the drive unit. The separation chamber 2 shown in FIG. 2 in top view is a disposable chamber made from transparent plastic. It has a central rotation axis 3 which bears, via radial crosspieces 4, an essentially annular separation channel 5 for receiving the whole blood which is separated into its constituents by rotation of the chamber. When the chamber 2 is inserted into the drive unit 1 of the centrifuge, the outer teeth 6 of the rotation axis 3 engage with the teeth of driving means, not shown in the figures, of the drive unit 1, so that the separation chamber 2 can be set rotating.

The outer edge region of the chamber 2 adjacent to the outer wall of the separation channel 5 is divided, by a plurality of ribs 7 arranged circumferentially distributed, into individual segments 8 which, apart from a single chamber segment 8', all lie in a horizontal plane, i.e. in a plane running transversely relative to the axis of rotation. The chamber segments 8 form a scanning region (FIG. 5) which extends annularly around the rotation axis 3 of the chamber 2. They act like a semi-transparent mirror so that a light beam striking the segments is partially reflected. The chamber segment 8' (FIG. 4), inclined downwards by about 20° relative to the horizontal plane, forms a marker element which identifies a reference position of the chamber.

The centrifuge also has a phase boundary detection device, not shown in the figures, which determines the exact position of the phase boundary between the separated blood components in the separation channel 5 of the chamber 2 and controls the delivery rate of the pumps connected to the chamber. This type of phase boundary detection device is described in EP-A-0 116 716. In order to avoid repetition, reference is made to this printed publication.

Monitoring of the phase boundary takes place within a phase boundary window 10 (FIG. 1) of the separation chamber 2. In order to be able to determine the position of the phase boundary window, it is necessary to ascertain the instantaneous angular position of the chamber 2 set rotating by the drive unit 1 of the centrifuge. The scanning device 11 for recognizing the position of the separation chamber 2 is described below.

Figure 6:
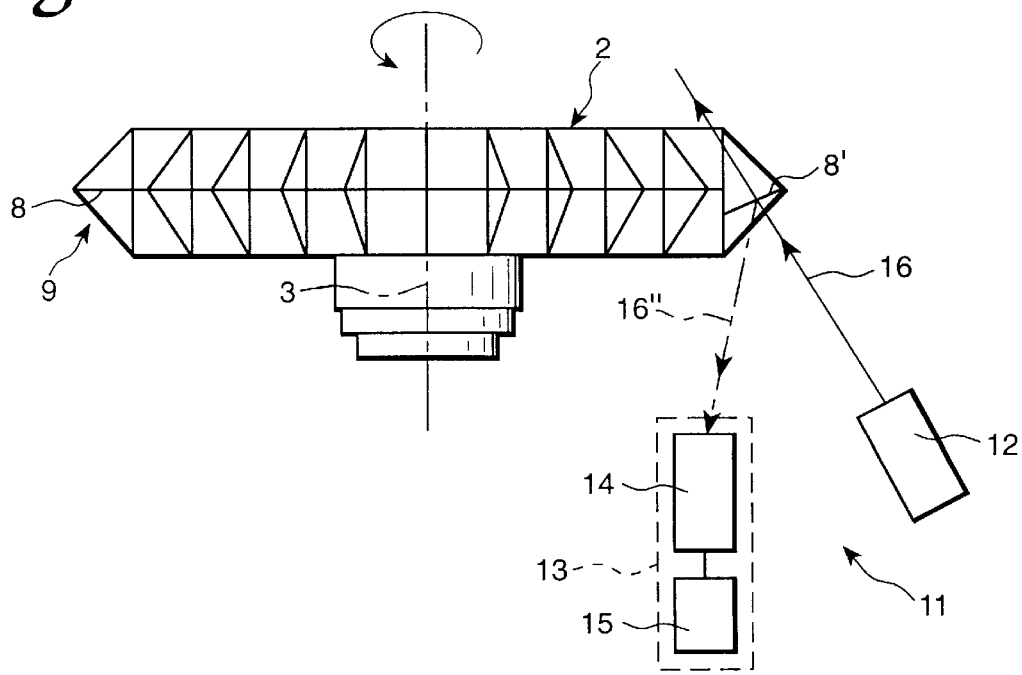

The scanning device 11 has a light source 12 and a detector device 13. The detector device 13 outlined in FIGS. 5 and 6 by dotted lines consists of a light receiver 14 and a downstream evaluation unit 15. A photodiode or a phototransistor can e.g. be used as light receiver. Appropriate lens arrangements can be provided for focusing the light beams. The light source 12 of the scanning device 11 is arranged in such a way that the light beam 16 originating from the light source strikes the scanning region 9 which extends annularly around the rotation axis 3 of the separation chamber 2, whilst the light receiver 14 is in the beam path of the light beam 16" reflected by the inclined chamber segment 8' (FIG. 6). When the light beam 16 strikes the horizontal chamber segments 8, it is reflected by another angle relative to the rotation axis so that the light beam 16' does not reach the light receiver 14 (FIG. 5). The light receiver 14 thus transmits a reference signal to the evaluation unit 15 only when the light beam strikes the marker element. The light receiver 14 is equipped with a suitable threshold value switch for detecting the reflected light beam. In the evaluation unit 15 the position of the separation chamber 2 and the instantaneous position of the phase boundary window 10 relative to the boundary detection device, which is arranged in fixed manner, is determined from the reference signal of the light receiver 14.

The light receiver 14 arranged below the separation channel 5 can not only be used for detecting the light beam 16" reflected at the marker element 8', but can also be used to recognize the position of the phase boundary. The receiver 14 can thus be used both for recognizing the position of the separation chamber 2 and for determining the position of the phase boundary.

Since, with the device according to the invention, it is not necessary to ensure the position in which the separation chamber 2 is inserted into the drive unit 1, faulty operation of the equipment is excluded. Centrifuge operation is also simplified, without the need to make major changes to the separation chamber.

What is claimed is:

1. A centrifuge comprising:
    a drive unit;
    a separation chamber selectively insertable into the drive unit as an exchangeable part and rotatable by the drive unit when so inserted, said separation chamber including a plurality of annularly disposed segments radially oriented with respect to an axis about which said chamber rotates;
    a marker element serving as a reference position indicator for said chamber relative to said drive unit, said marker element being formed by arranging one of said segments in a plane which is inclined with respect to a common plane which others of said segments lie; and
    a scanning device for detecting the position of the separation chamber, when rotated by the drive unit, by sensing the marker element.

2. A centrifuge according to claim 1, wherein the scanning device has a light source, the light from which strikes the separation chamber, and a detector device for detecting the change in distribution of light reflected by the separation chamber.

3. A centrifuge according to claim 1, wherein the scanning device has a light source from which light strikes the separation chamber and a detector device for detecting the change in distribution of light shining through the chamber.

4. A centrifuge according to claim 1, wherein the detector device is an optical detector arranged in a path of light reflected by the inclined segment.

5. A centrifuge according to claim 1, wherein the separation chamber is an essentially rotationally symmetrical body made from transparent material which has an essentially annular separation channel communicating with said radially oriented segments for receiving a fluid which is separated into its constituents by rotation of the separation chamber, and wherein a scanning region for detecting the marker element is provided in a plane running transversely relative to the axis of rotation of the separation chamber and extending along an outer region of the separation chamber adjacent to the separation channel.

6. A centrifuge according to claim 2, wherein the separation chamber is an essentially rotationally symmetrical body made from transparent material which has an essentially annular separation channel communicating with said radially oriented segments for receiving a fluid which is separated into its constituents by rotation of the separation chamber, and wherein a scanning region for detecting the marker element is provided in a plane running transversely relative to the axis of rotation of the separation chamber and extending along an outer region of the separation chamber adjacent to the separation channel.

7. A centrifuge according to claim 3, wherein the separation chamber is an essentially rotationally symmetrical body made from transparent material which has an essentially annular separation channel communicating with said radially oriented segments for receiving a fluid which is separated into its constituents by rotation of the separation chamber, and wherein a scanning region for detecting the marker element is provided in a plane running transversely relative to the axis of rotation of the separation chamber and extending along an outer region of the separation chamber adjacent to the separation channel.

* * * * *